United States Patent [19]

Edwards

[11] 4,239,781
[45] Dec. 16, 1980

[54] METHOD FOR TREATING SKIN AILMENTS

[76] Inventor: Roy Edwards, 1415 Highland Dr., Solana Beach, Calif. 92075

[21] Appl. No.: 35,604

[22] Filed: May 3, 1979

Related U.S. Application Data

[63] Continuation of Ser. No. 876,203, Feb. 9, 1978, abandoned.

[51] Int. Cl.³ .............................................. A61K 31/08
[52] U.S. Cl. .............................. 424/342; 424/DIG. 5
[58] Field of Search .......................... 424/342, DIG. 5

[56] References Cited

U.S. PATENT DOCUMENTS

| 3,729,568 | 4/1973 | Kligman | 424/318 |
| 3,949,087 | 4/1976 | Baoq et al. | 424/319 |
| 3,959,463 | 5/1976 | Nersesian | 424/70 |

OTHER PUBLICATIONS

Remington's Practice of Pharmacy, 11th Ed., 1956, pp. 341–343 & 646–648.

*Primary Examiner*—Leonard Schenkman
*Attorney, Agent, or Firm*—McDougall, Hersh & Scott

[57] ABSTRACT

A method for treating skin ailments comprising applying polyethylene glycol or other lower polyalkylene glycol to the ailing portion of the skin.

3 Claims, No Drawings

METHOD FOR TREATING SKIN AILMENTS

This is a continuation of application Ser. No. 876,203, filed Feb. 9, 1978, now abandoned.

This invention relates to ailments of the skin and to the treatment of same.

Ailments of the skin of the type capable of treatment in accordance with the practice of this invention include, amongst others, flaking of the skin, dandruff, athlete's foot, and eczema.

Such skin ailments have, in the past been treated with various ointments and the like compositions formulated by the physician or pharmaceutical houses to contain various chemicals, extracts and the like materials for topical application to the skin or with pills, capsules or injections containing various compounds believed to impart a beneficial effect to alleviate the skin ailment.

It has been found, in accordance with the practice of this invention that an effective treatment for such skin ailments can be effected by topical application to the affected portion of the skin of a composition in which the essential ingredient comprises a polyalkylene glycol such as polyethylene glycol, polypropylene glycol, polybutylene and the like lower alkylene polyglycols. The polyalkylene glycol, preferably polyethylene glycol, can range from a low molecular weight polyethylene glycol of liquid consistency such as in the molecular weight range of 200–1500 and preferably 400–1000 to a solid polyethylene glycol of high molecular weight such as polyethylene glycol of waxy consistency, of the type marketed by Union Carbide Corporation under the trademark CARBOWAX.

Such polyethylene glycols can be applied topically directly to the skin without dilution or admixture with other materials or they can be formulated for application as a liquid in admixture with an organic solvent, or as an emollient in admixture with oils such as mineral or vegetable oils, or as an ointment in admixture with various fillers such as zinc oxide, talc, diatomaceous earth and the like, or as a stick in admixture with gels or other thixatropic materials.

The skin treating compositions of this invention may contain skin care ingredients other than the polyalkylene glycols for softening the skin or to increase penetration into the skin or for other desirable beneficial effects during skin treatment in accordance with the practice of this invention.

By way of examples, the substantial elimination of dandruff can be achieved by the topical application of polyethylene glycol (M.W. 400) as a liquid with application made twice a day in an amount to wet the scalp with the liquid. The liquid is allowed to remain to wet the scalp for hours without harmful effect with the substantially complete elimination of dandruff or flaking of the skin within 2–5 treatments or within a few days.

In the treatment of skin rash or eczema, topical application to the affected portions of the skin can be made with an ointment containing 50 percent by weight polyethylene glycol (Molecular Weight 400–15,000) and 25 percent by weight zinc oxide and 25 percent by weight mineral oil, or by rubbing the affected portions of the skin with a stick formulated of Carbowax.

Polyethylene glycol, in liquid or solid form, or polypropylene glycol in liquid or solid form, alone or in admixture with talc can be applied in the treatment of athlete's foot to effect relief within two to four days by topical application twice a day, preferably before bed and before dressing in the morning and preferably after the affected portions have been cleansed.

Treatment of skin ailments with polyalkylene glycols, in accordance with the practice of this invention, is not only desirable because of its effectiveness, but also because such polyalkylene glycols are free of odor and relatively free of color so that the use thereof is not noticeable and the polyalkylene glycols readily wet the skin to enable access to the affected areas for immediate relief.

While such polyalkylene glycols may have been used as diluents or carriers in other pharmaceutical compositions, the discovery of the beneficial effect on skin ailments, even when used alone, was quite surprising and, of course, most desirable since such polyalkylene glycols can be easily applied without side effects and they represent a readily available low cost material.

I claim:

1. A method of treating skin ailments, comprising flaking of the skin, athlete's foot, dandruff and eczema consisting of topically applying to the portion of the skin in an amount to wet the skin, a composition consisting of a polyalkylene glycol as the active ingredient.

2. The method as claimed in claim 1 in which the polyalkylene glycol is polyethylene glycol.

3. The method as claimed in claim 1 in which the polyalkylene glycol is polypropylene glycol.

* * * * *